United States Patent
Fazzari et al.

(10) Patent No.: US 11,491,128 B2
(45) Date of Patent: *Nov. 8, 2022

(54) REVERSIBLE NITROXIDE DERIVATIVES OF NITROALKENES THAT MEDIATE NITROSATING AND ALKYLATING REACTIONS

(71) Applicant: University of Pittsburgh—Of the Commonwealth System of Higher Education, Pittsburgh, PA (US)

(72) Inventors: Marco Fazzari, Pittsburgh, PA (US); Bruce A. Freeman, Pittsburgh, PA (US); Francisco J. Schopfer, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 73 days.

This patent is subject to a terminal disclaimer.

(21) Appl. No.: 16/995,594

(22) Filed: Aug. 17, 2020

(65) Prior Publication Data
US 2020/0375936 A1 Dec. 3, 2020

Related U.S. Application Data

(63) Continuation of application No. 16/339,703, filed as application No. PCT/US2017/055154 on Oct. 4, 2017, now Pat. No. 10,765,652.
(Continued)

(51) Int. Cl.
*A61K 31/201* (2006.01)
*C07C 205/50* (2006.01)
(Continued)

(52) U.S. Cl.
CPC .............. *A61K 31/201* (2013.01); *A61P 1/04* (2018.01); *A61P 3/00* (2018.01); *A61P 3/04* (2018.01);
(Continued)

(58) Field of Classification Search
CPC .... A61K 31/20; A61K 31/201; C07C 205/50; C07C 205/51; A61P 9/08; A61P 3/00; A61P 13/12; A61P 29/00
See application file for complete search history.

(56) References Cited

U.S. PATENT DOCUMENTS 8,324,277 B2  12/2012  Freeman
8,735,449 B2  5/2014  Freeman
(Continued)

FOREIGN PATENT DOCUMENTS

WO  WO 2009/017802  2/2009
WO  WO 2010/014889  2/2010
(Continued)

OTHER PUBLICATIONS

PubChem CID 71410655 https://pubchem.ncbi.nlm.nih.gov/compound/71410655 (Year: 2013).*
(Continued)

*Primary Examiner* — Shengjun Wang
(74) *Attorney, Agent, or Firm* — Klarquist Sparkman, LLP (57) ABSTRACT

Various embodiments of this invention are directed to pharmaceutical compositions and methods for treating disease. The compositions of such embodiments include reversible nitroxide derivatives of nitroalkenes. The methods of various embodiments include administering an effective amount of any of these pharmaceutical compositions to a patient in need of treatment.

10 Claims, 5 Drawing Sheets

Related U.S. Application Data (60) Provisional application No. 62/404,354, filed on Oct. 5, 2016.

(51) Int. Cl.
| | | |
|---|---|---|
| *A61P 1/04* | (2006.01) | |
| *A61P 3/04* | (2006.01) | |
| *A61P 9/08* | (2006.01) | |
| *A61P 3/00* | (2006.01) | |
| *A61P 29/00* | (2006.01) | |
| *A61P 13/12* | (2006.01) | |
| *C07C 57/02* | (2006.01) | |

(52) U.S. Cl.
CPC ............... *A61P 9/08* (2018.01); *A61P 13/12* (2018.01); *A61P 29/00* (2018.01); *C07C 57/02* (2013.01); *C07C 205/50* (2013.01)

(56) References Cited

U.S. PATENT DOCUMENTS

| | | | |
|---|---|---|---|
| 9,066,902 | B2 | 6/2015 | Freeman et al. |
| 9,700,534 | B2 | 7/2017 | Freeman et al. |
| 9,750,725 | B2 | 9/2017 | Freeman et al. |
| 10,213,417 | B2 | 2/2019 | Freeman et al. |
| 10,258,589 | B2 | 4/2019 | Freeman et al. |
| 2015/0018417 | A1 | 1/2015 | Freeman et al. |
| 2019/0091186 | A1 | 3/2019 | Freeman et al. |

FOREIGN PATENT DOCUMENTS

| | | |
|---|---|---|
| WO | WO 2011/014261 | 2/2011 |
| WO | WO 2011/143587 | 11/2011 |
| WO | WO 2013/116753 | 8/2013 |
| WO | WO 2017/151938 | 9/2017 |
| WO | WO 2018/067705 | 4/2018 |

OTHER PUBLICATIONS

Baker et al., "Convergence of nitric oxide and lipid signaling: anti-inflammatory nitro-fatty acids," *Free Radical Biology and Medicine*, 46(8): 989-1003, Apr. 15, 2009.

Bonacci et al., "Conjugated linoleic acid is a preferential substrate for fatty acid nitration," *J. Biol. Chem.*, vol. 287, pp. 44071-44082, Nov. 9, 2012.

Extended European Search Report issued for EPC Application No. 17859123 dated Apr. 29, 2020.

Grossi et al., "The chemistry of peroxynitrite: involvement of an ET process in the radical nitration of unsaturated and aromatic systems," *Eur. J. Org. Chem.*, 2001(4): 741-748, Jan. 23, 2001.

International Search Report and Written Opinion issued for International Application No. PCT/US2017/055154 dated Jan. 18, 2018.

Manini et al., "Chemistry of nitrated lipids: remarkable instability of 9-nitrolinoleic acid in neutral aqueous medium and a novel nitronitrate ester product by concurrent autooxidation/nitric oxide-release pathways," *The Journal of Organic Chemistry*, 73(19): 7517-7525, Sep. 4, 2008.

Napolitano et al., "The acid-promoted reaction of ethyl linoleate with nitrite. New insights from 15N-labelling and peculiar activity of a model skipped diene," *Tetrahedron*, 58(25): 5061-5067, Jun. 17, 2002.

U.S. Appl. No. 16/239,425, filed Jan. 3, 2019.

U.S. Appl. No. 16/280,704, filed Feb. 20, 2019.

Woodcock et al., "Biomimetic nitration of conjugated linoleic acid: formulation and characterization of naturally occurring conjugated nitrodienes," *The Journal of Organic Chemistry*, 79(1): 25-33, Dec. 19, 2013.

* cited by examiner

REVERSIBLE NITROXIDE DERIVATIVES OF NITROALKENES THAT MEDIATE NITROSATING AND ALKYLATING REACTIONS

CROSS REFERENCE TO RELATED APPLICATIONS

This application is a continuation of U.S. application Ser. No. 16/339,703, filed on Apr. 4, 2019, which is the U.S. National Stage of International Application No. PCT/US2017/055154, filed Oct. 4, 2017, which was published in English under PCT Article 21(2), which application in turn claims the benefit of U.S. Provisional Application No. 62/404,354, filed Oct. 5, 2016, which is herein incorporated by reference in its entirety.

ACKNOWLEDGEMENT OF GOVERNMENT SUPPORT

This invention was made with government support under grant Nos. AT006822, HL058115, and HL064937 awarded by the National Institutes of Health. The United States government has certain rights in the invention.

SUMMARY

Embodiments of the invention are directed to unsaturated fatty acids having an electron withdrawing group, a leaving group, and a carbon-carbon double bond disposed between the electron withdrawing group and the leaving group. In some embodiments, the unsaturated fatty acids may be nitrogen oxides of nitroalkenes having electron withdrawing group may be a nitro group (—NO) and the leaving group may be a nitrogen oxide, such as nitrate (—$ONO_2$) or nitrite (—ONO). Various embodiments of the invention are directed to pharmaceutical compositions comprising an effective amount of a reversible nitrogen oxides of nitroalkenes. Other embodiments of the invention are directed to methods for treating inflammation, obesity, metabolic syndrome, acute kidney disease, chronic kidney disease, and inducing vasodilation including the step of delivering nitrogen oxides by administering an effective amount of reversible nitrogen oxides of nitroalkenes to a subject in need thereof.

DETAILED DESCRIPTION

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

The term "derivative" or "derivatives" refers to a compound that is derived from a similar compound, or a compound that can be imagined to arise from another compound, if one or more atoms are replaced with another atom or group of atoms.

The term "biological sample" refers to tissue, cells, fluids, cellular extract, homogenized tissue extract, or a mixture of one or more enzymes in a suitable physiologically acceptable carrier, such as a mixture that includes without limitation liposomes, albumin and lipoproteins.

The compounds of the invention can exist in various isomeric forms, including configurational, geometric, and conformational isomers, as well as existing in various tautomeric forms, particularly those that differ in the point of attachment of a hydrogen atom and in some constitutional isomers, in which there are variable numbers of repeating units. The term "isomer" is intended to encompass all isomeric forms of a compound of this invention, including tautomeric forms of the compound.

Certain compounds described here may have asymmetric centers and therefore exist in different enantiomeric and diastereomeric forms. The compounds of the invention can be in the form of an optical isomers or a diastereomers. Accordingly, the invention encompasses compounds in the form of their optical isomers, diastereoisomers and mixtures thereof, including a racemic mixture. Optical isomers of the compounds of the invention can be obtained by known techniques such as asymmetric synthesis, chiral chromatography, simulated moving bed technology or via chemical separation of stereoisomers through the employment of optically active resolving agents.

The term "prodrug" denotes a derivative of a compound that can hydrolyze, oxidize, or otherwise react under biological conditions, in vitro or in vivo, to provide an active compound, particularly a compound of the invention. Examples of prodrugs include, but are not limited to, derivatives and metabolites of a compound of the invention that include biohydrolyzable groups such as nitrates, nitrites, nitroso compounds, biohydrolyzable amides, biohydrolyzable esters, biohydrolyzable carbamates, biohydrolyzable thiolates, biohydrolyzable thioesters, biohydrolyzable selenides, and biohydrolyzable phosphate analogues (e.g., monophosphate, diphosphate or triphosphate). For instance, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by BURGER'S MEDICINAL CHEMIS- TRY AND DRUG DISCOVERY 6th ed. (Wiley, 2001) and DESIGN AND APPLICATION OF PRODRUGS (Harwood Academic Publishers Gmbh, 1985).

As used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 100 mg means in the range of 90 mg-110 mg.

"Administering" when used in conjunction with a therapeutic means to administer a therapeutic to a patient whereby the therapeutic positively impacts the tissue to which it is targeted. Thus, as used herein, the term "administering", when used in conjunction with a compound described herein can include, but is not limited to, providing a compound described herein to a subject systemically by, for example, intravenous injection, whereby the therapeutic reaches the target tissue. "Administering" a composition may be accomplished by, for example, injection, oral administration, topical administration, or by these methods in combination with other known techniques. Administering may be self-administration, wherein the subject in need of such treatment administers a therapeutic or administering may be by a medical or other health care professional or a caretaker of the subject in need of such treatment.

The term "animal," "patient," or "subject" as used herein includes, but is not limited to, humans and non-human vertebrates such as wild, domestic and farm animals.

The term "improves" is used to convey that the present invention changes either the characteristics and/or the physical attributes of the tissue to which it is being provided, applied or administered. The term "improves" may also be used in conjunction with a diseased state such that when a diseased state is "improved" the symptoms or physical characteristics associated with the diseased state are diminished, reduced or eliminated.

The term "inhibiting" includes the administration of a compound of the present invention to prevent the onset of the symptoms, alleviate the symptoms, or eliminate the disease, condition, disorder or a symptom or symptoms thereof.

By "pharmaceutically acceptable", it is meant the carrier, diluent or excipient must be compatible with the other ingredients of the formulation and not deleterious to the recipient thereof.

As used herein, the term "therapeutic" means an agent utilized to discourage, combat, ameliorate, improve, prevent, inhibit, block or reverse an unwanted condition, disease or symptom of a patient as may be indicated by the particular embodiment. In part, embodiments of the present invention are directed to inflammatory conditions, obesity, metabolic syndrome, acute kidney disease, chronic kidney disease, atherogenesis, adipogenesis, neointimal proliferation, kidney injury after ischaemia/reperfusion (I/R) and xenobiotic injury, focal myocardial I/R injury, Ang II-induced systemic hypertension, pulmonary hypertension, cardiac, kidney, hepatic and pulmonary fibrosis, inflammatory bowel disease, nociception, stroke, motor neuron degeneration, diabetes, asthma, COPD, metabolic syndrome, multiple sclerosis, hypertriglyceridemia, fatty liver disease and autoimmune diseases.

A "therapeutically effective amount" or "effective amount" of a composition is a predetermined amount calculated to achieve the desired effect, i.e., to discourage, combat, ameliorate, improve, prevent, inhibit, block, or reverse an unwanted condition, disease or symptom of a patient as may be indicated by the particular embodiment. For example, a "therapeutically effective amount" as recited in a "method of treating" embodiment is a predetermined amount calculated to achieve the desired treatment effect, i.e., to discourage, combat, ameliorate, or improve an unwanted condition, disease or symptom. For example, a "therapeutically effective amount" as recited in a "method of preventing" embodiment is a predetermined amount calculated to achieve the desired treatment effect, i.e., to prevent or inhibit or block an unwanted condition, disease or symptom prior to its occurrence. In part, embodiments of the present invention are directed to inflammatory conditions, cancer, cardiovascular disease, high blood pressure, stroke, obesity, and diabetes. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the effective amount administered will be determined by the physician in the light of the relevant circumstances including the condition to be treated, the choice of compound to be administered, and the chosen route of administration, and therefore, the dosage ranges included herein are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," "treating," "ameliorate," "improve," or "promote" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms of the condition, disorder or disease; diminishment of the extent of the condition, disorder or disease; stabilization (i.e., not worsening) of the state of the condition, disorder or disease; maintain the condition, disorder or disease; delay in onset or slowing of the progression of the condition, disorder or disease; and remission (whether partial or total), whether detectable or undetectable, or enhancement or improvement of the condition, disorder or disease. Amelioration or promotion includes eliciting a clinically significant response without excessive levels of side effects.

Generally speaking, the term "tissue" refers to any aggregation of similarly specialized cells which are united in the performance of a particular function.

Nitro-fatty acids are compounds that are typically elevated in response to oxidative and nitrative stress or in the diet. These compounds have been implicated as potential anti-oxidative and anti-inflammatory therapeutics for a variety of conditions such as inflammatory conditions, obesity, metabolic syndrome, acute kidney disease, chronic kidney disease, atherogenesis, adipogenesis, neointimal proliferation, kidney I/R and xenobiotic injury, focal myocardial I/R injury, Ang II-induced systemic hypertension, pulmonary hypertension, cardiac, renal, and pulmonary fibrosis, inflammatory bowel disease, nociception, stroke, motor neuron degeneration, diabetes, asthma, and COPD. Nitro-oleic acid ($NO_2$-OA), in particular, is the subject of many studies. Nitro-oleic acid affects many regulatory pathways, including Nrf2, NF-κB, heat shock factor (HSF), PPAR-γ, which leads to anti-oxidant and anti-inflammatory effects. Also, nitro-oleic acid leads to direct enzyme inhibition of xanthine oxidase, soluble epoxide hydrolase, GAPDH and 5-lipoxygenase. Additional pathways modified by nitro fatty acids include: extracellular signal-regulated kinases, Jun amino-terminal kinases, p38 mitogen-activated protein kinases, signal transducer and activator of transcription 1, TRP channels, TNF receptor associated factor 6 and toll-like receptor 4. $NO_2$—CLA shares many of the actions of $NO_2$-OA including inhibition of Nf-kB, activation of Nrf2 and heat shock pathway and has potent anti-inflammatory actions.

Recent studies have reported that cardiovascular diseases (CVDs), cancer, stroke and diabetes are attributed in part to poor nutrition, accounting in the USA for >33 billion in medical costs and 9 billion in lost productivity annually. Moreover, in 2010, a total of 678,000 deaths of all the causes were attributable to suboptimal dietary habits, making this the leading causes of mortality in USA. In this regard, solid data supports that the Mediterranean diet limits inflammation and the development of CVDs, breast and colon cancer, obesity and other problems. While the benefits of the Mediterranean diet are well supported, it is unclear if a particular dietary constituent or the diet in toto is mediating downstream responses. The Mediterranean diet is characterized by consumption of fruits, vegetables and dairy products, providing antioxidants, unsaturated fats and the inorganic anions nitrite ($NO_2^-$) and nitrate ($NO_3^-$). From our and others observations, $NO_3^-$ is readily reduced to $NO_2^-$ via entero-salivary anaerobic bacterial metabolism and, then in the acidic conditions of the stomach, the protonation of $NO_2^-$ induces generation of a broad range of nitrogen oxides. This provides an environment for efficient nitration of unsaturated fatty acids and the endogenous formation of nitro fatty acids ($NO_2$—FA) and the newly identified reversible nitrogen oxides of nitroalkenes [$NO_2$—$NO_3$-FA].

Embodiments of the invention are generally directed to unsaturated fatty acids having an electron withdrawing group, a leaving group, and a carbon-carbon double bond disposed between the electron withdrawing group and the leaving group. In some embodiments, the unsaturated fatty acids may be nitrogen oxides of activated fatty acids in which the electron withdrawing group is nitro (—NO), and in particular embodiments, the unsaturated fatty acids may be nitrogen oxides of nitroalkenes in which the electron withdrawing group is a nitro group (—NO) and the leaving group may be a nitrogen oxide, such as nitrate (—$ONO_2$) or nitrite (—ONO). As used herein an "activated fatty acid" refers to a fatty acid having at least one electron withdrawing group covalently bound to a saturated or unsaturated aliphatic chain of a fatty acid. Such activated fatty acids may include an aliphatic chain substituted by any number of electron withdrawing groups at any number of positions and such electron withdrawing groups may or may not be associated with a carbon-carbon double bond. Similarly, the reversible nitrogen oxide derivatives of nitroalkenes may include an aliphatic chain having any number of double bonds, which may or may not be associated with an electron withdrawing group. In certain embodiments, leaving group may be positioned at the beta (β) carbon, gamma (γ) carbon, or delta (δ) carbon of the unsaturated aliphatic chain, where the electron withdrawing group is attached to the alpha (α) carbon.

For example, the compounds of some embodiments may be of the general Formula I:

(I)

wherein $R^1$ is —H or any electron withdrawing groups including, but not limited to —COH, —COR, —COOH, —COOR, —Cl, —F, —Br, —I, —$CF_3$, —CN, —$SO_3$—, —$SO_2R$, —$SO_3H$, —$NH_3^+$, —$NH_2R^+$, —$NHR_2^+$, —$NR_3^+$ and —$NO_2$; $R^2$ is a leaving group including, but not limited to, —OC(O)($C_{1-4}$), —$ONO_2$, —OPO(OH)$_2$, —$OSO_3$, and other inorganic esters; $X^1$ and $X^2$ are —H —COH, —COR, —COOH, —COOR, —$COCF_3$, and —$CF_2R$; and m and n are, independently, an integer from 1 to 10, and compositions containing the same.

Compounds in still other embodiments, may be of general Formula II:

(II)

wherein $R^1$ is —H or any electron withdrawing groups including, but not limited to —COH, —COR, —COOH, —COOR, —Cl, —F, —Br, —I, —$CF_3$, —CN, —$SO_3$—, —$SO_2R$, —$SO_3H$, —$NH_3^+$, —$NH_2R^+$, —$NHR_2^+$, —$NR_3^+$ and —$NO_2$; $R^2$ is a leaving group including, but not limited to, —OC(O)($C_{1-4}$), —$ONO_2$, —OPO(OH)$_2$, —$OSO_3$, and other inorganic esters; $X^1$ and $X^2$ are —H —COH, —COR, —COOH, —COOR, —$COCF_3$, and —$CF_2R$; and m and n are, independently, an integer from 1 to 10, and compositions containing the same.

In certain embodiments, the nitrogen oxides of nitroalkenes may be of the general Formula III:

(III)

wherein m and n are, independently, an integer from 1 to 10, and compositions containing the same.

In some embodiments, the nitrogen oxides of nitroalkene may be of Formula IV:

(IV)

The reversible nitrogen oxides of nitroalkene of Formula III is (E)-9-nitro-12-(nitrooxy)octadec-10-enoic acid, reversible nitrogen oxides of conjugated linoleic acid, or $NO_2$—$NO_3$-CLA.

In such embodiments, the electron withdrawing group may be positioned in either E or Z configuration in the original double bond or in either R or S absolute stereochemistry at an $sp^3$ chiral/stereogenic center. For example, in one embodiment, a reversible nitroxide derivative of nitroalkenes may have one electron withdrawing group, and in another, a reversible nitroxide derivative of nitroalkenes may be substituted with multiple electron withdrawing groups at multiple positions along the hydrocarbon chain. While the reversible nitroxide derivatives of nitroalkenes of the invention may have an electron withdrawing group positioned at any carbon along the aliphatic hydrocarbon chain between the carboxy terminal carbon to the terminal methyl (ω-position), in some embodiments, the electron withdrawing group may be positioned within about 3 carbons of either the carboxy terminal carbon and/or the methyl terminal carbon, and in other embodiments, the electron withdrawing group may be positioned within 5 carbons of either of the carboxy terminal carbon and/or the methyl terminal carbon. In still other embodiments, the electron withdrawing group may be positioned within 7 carbons of either of the carboxy terminal carbon and/or the methyl terminal carbon, and in further embodiments, the electron withdrawing group may be positioned within 9 carbons of either of the carboxy terminal carbon and/or the methyl terminal carbon.

In certain embodiments, the electron withdrawing group may be positioned on a carbon originating from a double bond of the activated fatty acid forming an "electron withdrawing vinyl" group. The electron withdrawing group of such vinyl groups may be on either side of the double bond. Fatty acids encompassed by embodiments of the invention may have one or more than one electron withdrawing vinyl groups at any carbon on the aliphatic hydrocarbon chain, and there are several ways that an unsaturated fatty acid can have one electron-withdrawing group. In one embodiment, a reversible nitrogen oxides of oleic acid (octadec-9-enoic acid) which originates from an 18 carbon, ω-9 fatty acid with one double bond (denoted "18:1") between the 9h (C-9) and 10th (C-10) carbons, may have an electron withdrawing group at either C-9 or C-10, and a leaving group at the alternate position. In another exemplary embodiment, a reversible nitrogen oxides of linoleic acid (octadeca-9,12,-dienoic acid), which originated from an 18 carbon, ω-6 fatty acid with two double bonds (denoted "18:2") between the ω-6 (C-13) and -7 (C-12) carbons and the ω-9 (C-10) and 10 (C-9) carbons, may have an electron withdrawing group at C-9 or C-10, or C-12 or C-13, a leaving group at the corresponding alternate neighboring position, and at least one carbon-carbon double bond positioned between the electron withdrawing group and the leaving group. In another embodiment, a reversible nitrogen oxides of linoleic acid may have an electron withdrawing group at C-9 or C-10, or C-12 or C-13, a leaving group at the corresponding alternate neighboring position, and at least one carbon-carbon double bond adjacent to the leaving group. Similarly, other polyunsaturated fatty acids, originally having 3, 4, 5, 6 or more double bonds, can have one electron withdrawing at either position on any of the original double bond carbons, and a leaving group at the corresponding alternate position, with a carbon-carbon double bond between the electron withdrawing group and the leaving group including all possible permutations of positions and electron withdrawing groups.

The term "electron-withdrawing group" is recognized in the art and denotes the tendency of a substituent to attract valence electrons from neighboring atoms, i.e., the substituent is electronegative with respect to neighboring atoms. The term "nucleophile" or "electron-donating group" is recognized in the art and denotes the tendency of a substituent to donate excess valence electrons from neighboring atoms, i.e., the substituent is electropositive with respect to neighboring atoms. A quantification of the level of electron withdrawing capability is given by the Hammett sigma (σ) constant (see, e.g., J. March, Advanced Organic Chemistry, McGraw Hill Book Company, New York, (1977 edition) pp. 251-259). The Hammett constant values are generally negative for electron donating groups and positive for electron withdrawing groups. For example the Hammet constant for para substituted $NH_2$ (σ[P]) is about −0.7 and the σ[P] for a nitro group is about +0.8.

Embodiments of the invention encompass any known electron withdrawing group. For example, electron-withdrawing groups may include, but are not limited to, aldehyde (—COH), acyl (—COR), carboxylic acid (—COOH), ester (—COOR), halides (—Cl, F, —Br, etc.), fluoromethyl (—$CF_3$), fluoroalkyl (—$CF_n$—$H_{2-n}R$), cyano (—CN), sulfoxide (—SOR), sulfonyl (—$SO_2R$), sulfonate ($SO_3R$), 1°, 2° and 3° ammonium (—$NR_3^+$), and nitro (—$NO_2$) where each R may, independently, be hydrogen, methyl, or $C_2$ to $C_6$ alkyl, alkenyl, or alkynyl. In some embodiments, the electron withdrawing group may be a strong electron withdrawing group having a σ of at least about 0.2, and in certain embodiments, the electron withdrawing group may form a dipole. For example, in particular embodiments, the electron withdrawing group may be a nitro, ammonium or sulfonyl.

The term "leaving group" is recognized in the art and denotes the tendency of a substituent to leave a parent molecule with a pair of electrons during heterolytic bond cleavage. Leaving groups encompassed by the invention include, for example, —OC(O)($C_{1-4}$), —$ONO_2$, —OPO$(OH)_2$, —$OSO_3$, other inorganic esters, and the like.

The fatty acids of embodiments may be any unsaturated and polyunsaturated fatty acid known in the art. The term "fatty acid" describes aliphatic monocarboxylic acids. Various embodiments include activated fatty acids having an aliphatic hydrocarbon chain identical or similar to identified, naturally occurring fatty acids. For example, aliphatic hydrocarbon chains of known naturally occurring fatty acids are generally unbranched and contain an even number of from about 4 to about 24 carbons, and others include fatty acids having from 12 to 18 carbons in the aliphatic hydrocarbon chain. In still other embodiments, fatty acids may have greater than 24 carbons in the aliphatic hydrocarbon chain. Embodiments of the invention encompass such naturally occurring fatty acids as well as non-naturally occurring fatty acids, which may contain an odd number of carbons and/or a non-naturally occurring linker including heteroatoms. Thus, some embodiments of the invention include fatty acids having an odd number of carbons of, for example, from 5 to 23 carbons, and in other embodiments, from 11 to 17 carbons. In yet other embodiments, the fatty acids of embodiments may have greater than 23 carbons. The naturally and non-naturally occurring fatty acids of the invention may also be branched at one or more location along the hydrocarbon chain, and in various embodiments, each branch may include an aliphatic hydrocarbon chain of from 1 to 24 carbons, 2 to 20 carbons or 4 to 18 carbons wherein each branch may have an even or odd number of carbons.

The aliphatic hydrocarbon chain of fatty acids of various embodiments may be unsaturated or polyunsaturated. The term "unsaturated" refers to a fatty acid having a aliphatic hydrocarbon chain that includes at least one double bond and/or substituent. In contrast, a "saturated" hydrocarbon chain does not include any double bonds or substituents. Thus, each carbon of the hydrocarbon chain is 'saturated' and has the maximum number of hydrogens. "Polyunsaturated," generally, refers to fatty acids having hydrocarbon chains with more than one double bond. The double bonds of the unsaturated or polyunsaturated fatty acids of various embodiments may be at any location along the aliphatic hydrocarbon chain and may be in either cis or trans configuration. The term "cis," refers to a double bond in which carbons adjacent to the double bond are on the same side and the term "trans" refers to a double bond in which carbons adjacent to the double bond are on opposite sides. Typically "cis" is the same as Z, and "trans" is the same as E but sometimes the IUPAC rules for naming compounds will give the opposite of this for non-carbon substituents, which is the typical case in nitroalkenes. For example, a nitroalkene can have the two carbon groups "cis" but the two groups that take priority for the naming of compounds (a nitro group on one carbon of the alkene and a carbon group on the other carbon of the alkene) are on opposite sides and thus are E. Therefore the nitroalkene analog of a "cis" double bond is termed an E nitroalkene. Similarly, the nitroalkene analog of a "trans" double bond is termed a Z nitroalkene. Without wishing to be bound by theory, double bonds in cis configuration along the carbon chain (cis carbon chain but E nitroalkene) may induce a bend in the hydrocarbon chain. Double bonds in "trans," configuration along the carbon chain (trans carbon chain but Z nitroalkene) may not cause the hydrocarbon chain to bend. Embodiments of the invention may include reversible nitroxide derivatives of nitroalkenes having double bonds in either E or Z configuration, and encompass compositions that may include combinations of cis and trans containing reversible nitroxide derivatives of nitroalkenes and regioisomers of the reversible nitroxide derivatives of nitroalkenes.

Many unsaturated and polyunsaturated fatty acids have been identified and are known to be naturally occurring. Such unsaturated or polyunsaturated naturally occurring fatty acids, generally, include an even number of carbons in their aliphatic hydrocarbon chain. For example, a naturally occurring unsaturated or polyunsaturated fatty acid may have, 4, 6, 8, 10, 12, 14, 16, 18, 20, 22 and so on carbons and may include omega ($\omega$)-3, $\omega$-5, $\omega$-6, $\omega$-7, $\omega$-9 carbon-carbon double bonds. Any such fatty acid may be useful in embodiments of the invention. The symbol '$\omega$' is used to refer to the terminal methyl carbon of the aliphatic hydrocarbon chain. The placement of the double bond of the $\omega$-X fatty acid is the carbon-carbon bond X number of carbons from the $\omega$ carbon. For example, an $\omega$-6 fatty acid has a double bond between the $6^{th}$ and 7th carbons counting backward from the $\omega$-carbon and an $\omega$-3 fatty acid has a double bond between the 3rd and 4th carbons counting backward from the $\omega$-carbon. Various embodiments of the invention include nitrated $\omega$-3 fatty acids, including, but not limited to, linolenic acid, alphalinolenic acid, eicosapentanoic acid, docosapentaenoic acid, docosahexanoic acid and stearidonic acid; nitrated $\omega$-5 fatty acids including, but not limited to, myristoleic acid; nitrated $\omega$-6 fatty acids including, but not limited to, linoleic acid, gamma-linoleic acid, dihomo-gamma-linoleic acid and arachidonic acid; nitrated $\omega$-7 fatty acids including, but not limited to, conjugated linoleic and palmitoleic acid; and nitrated $\omega$-9 fatty acids including, but not limited to, oleic acid and erucic acid. Of course, the fatty acids of the invention may also be referred to using IUPAC nomenclature in which the placement of the double bond is determined by counting from the carbon of the carboxylic acid, and 'C—X' denotes the carbon in aliphatic hydrocarbons using IUPAC nomenclature wherein X is the number of the carbon counting from the carboxylic acid (including the carbonyl carbon itself). Embodiments of the invention also include synthetic equivalents to naturally occurring fatty acids and derivatives thereof.

Other embodiments of the invention include unsaturated or polyunsaturated non-naturally occurring fatty acids which may have an odd number of carbons such as, for example, 5, 7, 9, 11, 13, 15, 17, 19, 21 and so on. As in naturally occurring fatty acids, the one or more double bonds associated with non-naturally occurring fatty acids may be at any position along the aliphatic hydrocarbon chain, and the double bonds may be in either cis or trans configuration. In yet other embodiments, the non-naturally occurring fatty acids may include one or more linker groups, which interrupt the aliphatic hydrocarbon chain. For example, in some embodiments, activated fatty acids may have one or more non-carbon-carbon linkage such as, for example, ester, ether, vinyl ether, thioether, amino, imine and the like at any position within the aliphatic hydrocarbon chain.

In still other embodiments, the carboxy-terminal end of the nitrogen oxides of activated fatty acid may be modified. For example, in some embodiments, the nitrogen oxides of activated fatty acid may include a glycerol associated with the carboxy-terminal end of the fatty acid to create a glycerolipid, and such glycerolipids may be mono-, di-, or tri-glycerides wherein at least one of the fatty acids of a di or tri-glyceride may be an activated-nitrate fatty acid and any remaining fatty acids may be a saturated or unsaturated fatty acid. Similarly, in other embodiments, a carbohydrate may be associated with the carboxy-terminal end of an nitrogen oxides activated fatty acid to form a glycolipid. In such embodiments, any carbohydrate known in the art may be a carbohydrate moiety of a glycolipid including, but not limited to, galactose and glucose. In yet other embodiments, a carbohydrate may be associated with a glyceride which is associated with the carboxy-terminal end of an activated-nitrate fatty acid to form a glycero-glycolipid, which may have one or two activated fatty acids associated with the glycero-portion of the glycero-glycolipid and, in embodiments in which only one activated fatty acid is associated with the glycero-glycolipid, the remaining position on the glycerol may include a saturated or unsaturated fatty acid or hydrogen, alkyl, or a functional group such as, for example, alcohol, amine, phosphate, phosphonic acid, thiol, sulfonic acid and the like. In certain embodiments, the carboxy-terminal end of the activated fatty acids of the invention may be associated with a phosphate to form a phospholipid. In such embodiments, the phosphate may be directly associated with the fatty acid through the carboxy-terminus, or the phosphate may be associated with a di-glyceride wherein one or two activated fatty acids are attached glycerol moiety and, in embodiments where only one activated-nitrate the fatty acid is attached to the glycerol, remaining position on the glycerol may include a saturated or unsaturated fatty acid or hydrogen, alkyl, or a functional group such as, for example, alcohol, amine, phosphate, phosphonic acid, thiol, sulfonic acid and the like. In further embodiments, the carboxy-terminus of the activated fatty acid may be associated with a cholesterol or other sterol moiety. In yet other embodiments, the carboxy-terminal end may be modified by the covalent attachment of a secondary active agent. In the particular embodiments, carboxy-terminal modifications including a glycerol may not include a nitro group. Without wishing to be bound by theory, modification of the carboxy-terminal end of activated-nitrate fatty acids may enhance partitioning of the activated fatty acid after administration and may also improve resilience of the activated fatty acid by inhibiting beta-oxidation in mitochondria following administration.

In embodiments described herein, the therapeutically effective amount of a reversible nitroxide derivative of nitroalkenes is from about 5 milligrams to about 5000 milligrams. In the various embodiments described above, a therapeutically effective amount of a reversible nitroxide derivative of nitroalkenes may be as a daily dose or a single dose within a range of a lower limit amount and an upper limit amount. In some embodiments, the lower limit amount is about 5 mg, about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about, 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1500 mg, about 2000 mg, about 2500 mg, about 3000 mg, about 3500 mg, about 4000 mg, about 4500 mg. In some embodiments, the upper limit amount is about 5000 mg, about 4500 mg, about 4000 mg, about 3500 mg, about 3000 mg, about 2500 mg, about 2000 mg, about 1500 mg, 1000 mg, about 975 mg, about 950 mg, about 925 mg, about 900 mg, about 875 mg, about 850 mg, about 825 mg, about 800 mg, about 775 mg, about 750 mg, about 725 mg, about 700 mg, about 675 mg, about 650 mg, about 625 mg, about 600 mg, about 575 mg, about 550 mg, about 525 mg, about 500 mg, about 475 mg, about 450 mg, about 425 mg, about 400 mg, about 375 mg, about 350 mg, about 325 mg, about 300 mg, about 275 mg, about 250 mg, about 225 mg, about 200 mg, about 175 mg, about 150 mg, about 125 mg, about 100 mg, about 75 mg, or about 50 mg. In some embodiments, the daily dose may be any range between an upper and a lower limit of ranges previously disclosed. In some embodiments, the daily dose may be from about 25 mg to less than about 450 mg, about 25 mg to about 425 mg, about 25 mg to about 400 mg, about 25 mg to about 375 mg, about 25 mg to about 350 mg, about 25 mg to about 325 mg, about 25 mg to about 300 mg, about 25 mg to about 275 mg, about 25 mg to about 250 mg, about 25 mg to about 225 mg, about 25 mg to about 200 mg, about 25 mg to about 175 mg, or about 25 mg to about 150 mg. In some embodiments, the daily dose may be from about 50 mg to about 450 mg, about 75 mg to about 450 mg, about 100 mg to about 450 mg, about 150 mg to about 450 mg, about 175 mg to about 450 mg, about 200 mg to about 450 mg, about 225 mg to about 450 mg, about 250 mg to about 450 mg, or about 275 mg to about 450 mg.

In embodiments described herein, the daily dose as described above may be administered once per day. In embodiments described herein, the daily dose as described above may be administered in equal amounts twice per day. In embodiments described herein, the daily dose as described above may be administered in equal amounts three times per day. In embodiments described herein, the daily dose as described above may be administered in equal amounts four times per day.

In embodiments described herein, a therapeutically effective amount of a reversible nitroxide derivative of nitroalkenes may vary as treatment progresses. For example, the daily dose (or dosing regimen) may be increased or decreased as treatment proceeds through administration cycles, or the daily dosage may increase or decrease throughout administration.

The reversible nitroxide derivatives of nitroalkenes described above may be prepared as a pharmaceutically acceptable formulation. The term "pharmaceutically acceptable" is used herein to mean that the compound is appropriate for use in a pharmaceutical product. For example, pharmaceutically acceptable cations include metallic ions and organic ions. More preferred metallic ions include, but are not limited to, appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

Isomeric and tautomeric forms of reversible nitroxide derivatives of nitroalkenes of the invention as well as pharmaceutically acceptable salts of these compounds are also encompassed by the invention. Exemplary pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric and galacturonic acids.

Suitable pharmaceutically acceptable base addition salts used in connection with the reversible nitroxide derivatives of nitroalkenes of the invention include metallic ion salts and organic ion salts. Exemplary metallic ion salts include, but are not limited to, appropriate alkali metal (group Ia) salts, alkaline earth metal (group IIa) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

In embodiments described herein, the compositions described can be used to deliver nitic oxide to a subject in need thereof. After ingestion the compound is broken down to release a nitric oxide molecule and a nitrated linoleic acid molecule. Without wishing to be bound by theory, the reversible nitroxide derivatives of nitroalkenes protects the delivery of 2 components, the nitric oxide and conjugated nitro linoleic acid or nitro oleic acid. Once digested the nitric oxide molecule will function as a vasodilator and the nitro linoleic acid will function to protect against metabolic and inflammatory stress. The delivery of the reversible nitroxide derivatives of nitroalkenes reduces the side effects of the gastrointestinal tract seen when ingesting nitric oxide or nitrated linoleic acid alone, including diarrhea, cramping irritation, inflammatory bowel disease, colitis, and ulcers.

In embodiments described herein, administering a therapeutically effective amount of a reversible nitroxide derivative of nitroalkenes, or a pharmaceutically acceptable salt thereof also includes administering a secondary agent. In embodiments described herein, the secondary agent may be selected from a group consisting of an ACE inhibitor, an angiotensin II receptor blocker, or a combination thereof. In some embodiments, the secondary agent may be elanapril. In embodiments described herein, the ACE inhibitor may be selected from a group consisting of perindopril, captopril, enalapril, lisinopril, ramipril, zofenopril, quinapril, benazepril, imidapril, trandolapril, cilazapril, and fosinopril. In embodiments described herein, the angiotensin II receptor blocker may be selected from a group consisting of azilsartan, candesartan, eprosartan, irbesartan, losartan, olmesartan, telmisartan, valsartan, fimasartan, and spironolactone.

In embodiments described herein, the therapeutically effective amount of a secondary agent is from about 2.5 milligrams to less than about 250 milligrams. In embodiments described herein, the daily dose of the secondary agent may be from about 5 mg to about 200 mg, about 10 mg to about 150 mg, about 15 mg to about 100 mg, about 20 mg to about 75 mg, about 25 mg to about 50 mg, or about 30 mg to about 40 mg.

The reversible nitroxide derivatives of nitroalkenes of the invention can be administered in any conventional manner by any route where they are active. Administration can be systemic or local. For example, administration can be, but is not limited to, parenteral, subcutaneous, intravenous, intramuscular, intraperitoneal, transdermal, oral, buccal, or ocular routes, or intranasally, intravaginally, by inhalation, by depot injections, or by implants. In embodiments described herein, the administration may be parenteral or intravenous, all in the presence or absence of stabilizing additives that favor extended systemic uptake, tissue half-life and intracellular delivery. Thus, modes of administration for the compounds of the present invention (either alone or in combination with other pharmaceuticals) can be injectable (including short-acting, depot, implant and pellet forms injected subcutaneously or intramuscularly). In embodiments described herein, an injectable formulation including a reversible nitroxide derivative of nitroalkenes may be deposited to a site of injury or inflammation, such as, for example, the site of a surgical incision or a site of inflammation due to arthroscopy, angioplasty, stent placement, by-pass surgery and so on.

Various embodiments of the invention are also directed to a method for administering reversible nitroxide derivatives of nitroalkenes. Specific modes of administration may vary and may depend on the indication. The selection of the specific route of administration and the dose regimen may be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., the clinician). Those skilled in the art will appreciate that dosages may be determined with guidance, for example, from Goodman & Gilman's The Pharmacological Basis of Therapeutics, Ninth Edition (1996), Appendix II, pp. 1707-1711 or from Goodman & Gilman's The Pharmacological Basis of Therapeutics, Tenth Edition (2001), Appendix II, pp. 475-493 both of which are hereby incorporated by reference in their entireties. Furthermore, in determining the human equivalent dose from animal studies the U.S. Department of Health and Human Services Food and Drug Administration Center for Drug Evaluation and Research's publication can be used. http://www.fda.gov/downloads/drugs/guidancecomplianceregulatoryinformation/guidances/ucm07 8932.pdf.

Pharmaceutical formulations containing the compounds of the above invention and a suitable carrier can be in various forms including, but not limited to, solids, solutions, powders, fluid emulsions, fluid suspensions, semi-solids, and dry powders including an effective amount of a reversible nitroxide derivative of nitroalkenes of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, stabilizers, antioxidants, preservatives, and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Oilman's, The Pharmaceutical Basis of Therapeutics*, 6th Edition, MacMillan Publishing Co., New York (1980) both of which are hereby incorporated by reference in their entireties can be consulted.

The compounds of the present invention can be formulated for parenteral or intravenous administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids diluents such as oleic acid find use in the preparation of injectables. Additional fatty acids diluents that may be useful in embodiments of the invention include, for example, one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethyleneglycerol fatty ester, polyoxyethylene fatty alcohol ether, polyethoxylated sterol, polyethoxylated castor oil, polyethoxylated vegetable oil, and the like. In some embodiments, the fatty acid diluent may be a mixture of fatty acids. In some embodiments, the fatty acid may be a fatty acid ester, a sugar ester of fatty acid, a glyceride of fatty acid, or an ethoxylated fatty acid ester, and in other embodiments, the fatty acid diluent may be a fatty alcohol such as, for example, stearyl alcohol, lauryl alcohol, palmityl alcohol, palmitolyl acid, cetyl alcohol, capryl alcohol, caprylyl alcohol, oleyl alcohol, linolenyl alcohol, arachidonic alcohol, behenyl alcohol, isobehenyl alcohol, selachyl alcohol, chimyl alcohol, and linoleyl alcohol and the like and mixtures thereof.

Other embodiments of the invention include reversible nitroxide derivatives of nitroalkenes prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

In embodiments described herein, the therapeutically effective amount of the reversible nitroxide derivatives of nitroalkenes is in a pharmaceutical composition. Preparation of a reversible nitroxide derivative of nitroalkenes in solid dosage form may vary. For example, in one embodiment, a liquid or gelatin formulation of the reversible nitroxide derivatives of nitroalkenes may be prepared by combining the reversible nitroxide derivatives of nitroalkenes with one or more fatty acid diluent, such as those described above, and adding a thickening agent to the liquid mixture to form a gelatin. The gelatin may then be encapsulated in unit dosage form to form a capsule. In another exemplary embodiment, an oily preparation of a reversible nitroxide derivative of nitroalkenes prepared as described above may be lyophilized to form a solid that may be mixed with one or more pharmaceutically acceptable excipient, carrier or diluent to form a tablet, and in yet another embodiment, the reversible nitroxide derivatives of nitroalkenes of an oily preparation may be crystallized to from a solid which may be combined with a pharmaceutically acceptable excipient, carrier or diluent to form a tablet.

Further embodiments which may be useful for oral administration of reversible nitroxide derivatives of nitroalkenes include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents.

In still further embodiments, reversible nitroxide derivatives of nitroalkenes of the invention can be formulated as a depot preparation. Such long acting formulations can be administered by implantation (for example, subcutaneously or intramuscularly) or by intramuscular injection. Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Other suitable diluents for injectable formulations include, but are not limited to those described below:

Vegetable oil: As used herein, the term "vegetable oil" refers to a compound, or mixture of compounds, formed from ethoxylation of vegetable oil, wherein at least one chain of polyethylene glycol is covalently bound to the vegetable oil. In some embodiments, the amount of ethoxylation can vary from about 2 to about 200, about 5 to 100, about 10 to about 80, about 20 to about 60, or about 12 to about 18 of ethylene glycol repeat units. The vegetable oil may be hydrogenated or unhydrogenated. Suitable vegetable oils include, but are not limited to castor oil, hydrogenated castor oil, sesame oil, corn oil, peanut oil, olive oil, sunflower oil, safflower oil, soybean oil, benzyl benzoate, sesame oil, cottonseed oil, and palm oil. Other suitable vegetable oils include commercially available synthetic oils such as, but not limited to, Miglyol™ 810 and 812 (available from Dynamit Nobel Chemicals, Sweden) Neobee™ M5 (available from Drew Chemical Corp.), Alofine™ (available from Jarchem Industries), the Lubritab™ series (available from JRS Pharma), the Sterotex™ (available from Abitec Corp.), Softisan™ 154 (available from Sasol), Croduret™ (available from Croda), Fancol™ (available from the Fanning Corp.), Cutina™ HR (available from Cognis), Simulsol™ (available from CJ Petrow), EmCon™ CO (available from Amisol Co.), Lipvol™ CO, SES, and HS-K (available from Lipo), and Sterotex™ HM (available from Abitec Corp.). Other suitable vegetable oils, including sesame, castor, corn, and cottonseed oils, include those listed in R. C. Rowe and P. J. Shesky, Handbook of Pharmaceutical Excipients, (2006), 5th ed., which is incorporated herein by reference in its entirety. Suitable polyethoxylated vegetable oils, include but are not limited to, Cremaphor™ EL or RH series (available from BASF), Emulphor™ EL-719 (available from Stepan products), and Emulphor™ EL-620P (available from GAF).

Mineral oils: As used herein, the term "mineral oil" refers to both unrefined and refined (light) mineral oil. Suitable mineral oils include, but are not limited to, the Avatech™ grades (available from Avatar Corp.), Drakeol™ grades (available from Penreco), Sirius™ grades (available from Shell), and the Citation™ grades (available from Avater Corp.).

Castor oils: As used herein, the term "castor oil" refers to a compound formed from the ethoxylation of castor oil, wherein at least one chain of polyethylene glycol is covalently bound to the castor oil. The castor oil may be hydrogenated or unhydrogenated. Synonyms for polyethoxylated castor oil include, but are not limited to polyoxyl castor oil, hydrogenated polyoxyl castor oil, mcrogolglyceroli ricinoleas, macrogolglyceroli hydroxystearas, polyoxyl 35 castor oil, and polyoxyl 40 hydrogenated castor oil. Suitable polyethoxylated castor oils include, but are not limited to, the Nikkol™ HCO series (available from Nikko Chemicals Co. Ltd.), such as Nikkol HCO-30, HC-40, HC-50, and HC-60 (polyethylene glycol-30 hydrogenated castor oil, polyethylene glycol-40 hydrogenated castor oil, polyethylene glycol-50 hydrogenated castor oil, and polyethylene glycol-60 hydrogenated castor oil, Emulphor™ EL-7 19 (castor oil 40 mole-ethoxylate, available from Stepan Products), the Cremophore™ series (available from BASF), which includes Cremophore RH40, RH60, and EL35 (polyethylene glycol-40 hydrogenated castor oil, polyethylene glycol-60 hydrogenated castor oil, and polyethylene glycol-35 hydrogenated castor oil, respectively), and the Emulgin® RO and HRE series (available from Cognis PharmaLine) Other suitable polyoxyethylene castor oil derivatives include those listed in R. C. Rowe and P. J. Shesky, Handbook of Pharmaceutical Excipients, (2006), 5th ed., which is incorporated herein by reference in its entirety.

Sterol: As used herein, the term "sterol" refers to a compound, or mixture of compounds, derived from the ethoxylation of sterol molecule. Suitable polyethoyxlated sterols include, but are not limited to, PEG-24 cholesterol ether, Solulan™ C-24 (available from Amerchol); PEG-30 cholestanol, Nikkol™ DHC (available from Nikko); Phytosterol, GENEROL™ series (available from Henkel); PEG-25 phyto sterol, Nikkol™ BPSH-25 (available from Nikko); PEG-5 soya sterol, Nikkol™ BPS-5 (available from Nikko); PEG-10 soya sterol, Nikkol™ BPS-10 (available from Nikko); PEG-20 soya sterol, Nikkol™ BPS-20 (available from Nikko); and PEG-30 soya sterol, Nikkol™ BPS-30 (available from Nikko). As used herein, the term "PEG" refers to polyethylene glycol.

Polyethylene glycol: As used herein, the term "polyethylene glycol" or "PEG" refers to a polymer containing ethylene glycol monomer units of formula —O—CH2-CH2-. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400. Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

Propylene glycol fatty acid ester: As used herein, the term "propylene glycol fatty acid ester" refers to an monoether or diester, or mixtures thereof, formed between propylene glycol or polypropylene glycol and a fatty acid. Fatty acids that are useful for deriving propylene glycol fatty alcohol ethers include, but are not limited to, those defined herein. In some embodiments, the monoester or diester is derived from propylene glycol. In some embodiments, the monoester or diester has about 1 to about 200 oxypropylene units. In some embodiments, the polypropylene glycol portion of the molecule has about 2 to about 100 oxypropylene units. In some embodiments, the monoester or diester has about 4 to about 50 oxypropylene units. In some embodiments, the monoester or diester has about 4 to about 30 oxypropylene units. Suitable propylene glycol fatty acid esters include, but are not limited to, propylene glycol laurates: Lauroglycol™ FCC and 90 (available from Gattefosse); propylene glycol caprylates: Capryol™ PGMC and 90 (available from Gatefosse); and propylene glycol dicaprylocaprates: Labrafac™ PG (available from Gatefosse).

Stearoyl macrogol glyceride: Stearoyl macrogol glyceride refers to a polyglycolized glyceride synthesized predominately from stearic acid or from compounds derived predominately from stearic acid, although other fatty acids or compounds derived from other fatty acids may be used in the synthesis as well. Suitable stearoyl macrogol glycerides include, but are not limited to, Gelucire® 50/13 (available from Gattefosse).

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

Exemplary excipients or carriers for use in solid and/or liquid dosage forms include, but are not limited to:

Sorbitol: Suitable sorbitols include, but are not limited to, PharmSorbidex E420 (available from Cargill), Liponic 70-NC and 76-NC (available from Lipo Chemical), Neosorb (available from Roquette), Partech SI (available from Merck), and Sorbogem (available from SPI Polyols).

Starch, sodium starch glycolate, and pregelatinized starch include, but are not limited to, those described in R. C. Rowe and P. J. Shesky, Handbook of Pharmaceutical Excipients, (2006), 5th ed., which is incorporated herein by reference in its entirety.

Disintegrant: The disintegrant may include one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In various embodiments, the condition to be treated may be, but may not be limited to, arterial stenosis, burns, hypertension, obesity, metabolic syndrome, acute kidney disease, chronic kidney disease, neurodegenerative disorders, skin disorders, arthritis, autoimmune disease, autoinflammatory disease, lupus, Lyme's disease, gout, sepsis, hyperthermia, ulcers, enterocolitis, osteoporosis, viral or bacterial infections, cytomegalovirus, periodontal disease, glomerulonephritis, sarcoidosis, lung disease, chronic lung injury, respiratory distress, lung inflammation, fibrosis of the lung, asthma, acquired respiratory distress syndrome, tobacco induced lung disease, granuloma formation, fibrosis of the liver, graft vs. host disease, dyslipidemias, postsurgical inflammation, coronary and peripheral vessel restenosis following angioplasty, stent placement or bypass graft, acute and chronic leukemia, B lymphocyte leukemia, neoplastic diseases, arteriosclerosis, atherosclerosis, myocardial inflammation, psoriasis, immunodeficiency, disseminated intravascular coagulation, systemic sclerosis, amyotrophic lateral sclerosis, multiple sclerosis, Parkinson's disease, Alzheimer's disease, encephalomyelitis, edema, inflammatory bowel disease, hyper IgE syndrome, cancer metastasis or growth, adoptive immune therapy, reperfusion syndrome, radiation burns, and alopecia.

Certain embodiments are directed to therapeutic method including the step of administering an effective amount of an unsaturated fatty acid having an electron withdrawing group, a leaving group, and a carbon-carbon double bond disposed between the electron withdrawing group and the leaving group to a subject in need thereof. In some embodiments, the unsaturated fatty acids in such methods may be nitrogen oxides of activated fatty acids in which the electron withdrawing group is nitro (—NO), and in particular embodiments, the unsaturated fatty acids of such methods may be nitrogen oxides of nitroalkenes in which the electron withdrawing group is a nitro group (—NO) and the leaving group may be a nitrogen oxide, such as nitrate (—$ONO_2$) or nitrite (—ONO). In various embodiments, the effective amount fo the unsaturated fatty acid may be administered in a pharmaceutical composition containing and a pharmaceutically acceptable excipient, diluent, carrier, or combinations thereof.

Without wishing to be bound by theory, in such embodiments, the leaving group may be released from the unsaturated fatty acid, and the leaving group may provide treatment to the patient. For example, in embodiments in which the unsaturated fatty acid is a nitrogen oxide, the nitic oxide molecule is released from the unsaturated fatty acid, inducing vasodilation. In particular embodiments, the nitric oxide and a nitro group of a nitrogen oxides of nitroalkene may be released from the unsaturated fatty acid, inducing vasodilation. In other embodiments, a an activated fatty acid may be generated upon release of the leaving group, inducing anti-inflammatory activity.

The therapeutic methods of such embodiments may be used to treat a variety of disease indications including, for example, inflammation, obesity, metabolic syndrome, acute kidney disease, and chronic kidney disease. In certain embodiments, such methods may provide therapeutic effect while reducing such as, for example, diarrhea, cramping irritation, inflammatory bowel disease, colitis, and ulcers.

The present invention, thus generally described, will be understood more readily by reference to the following examples, which are provided by way of illustration and are not intended to be limiting of the present invention.

EXAMPLES

Example 1

Figure 1:
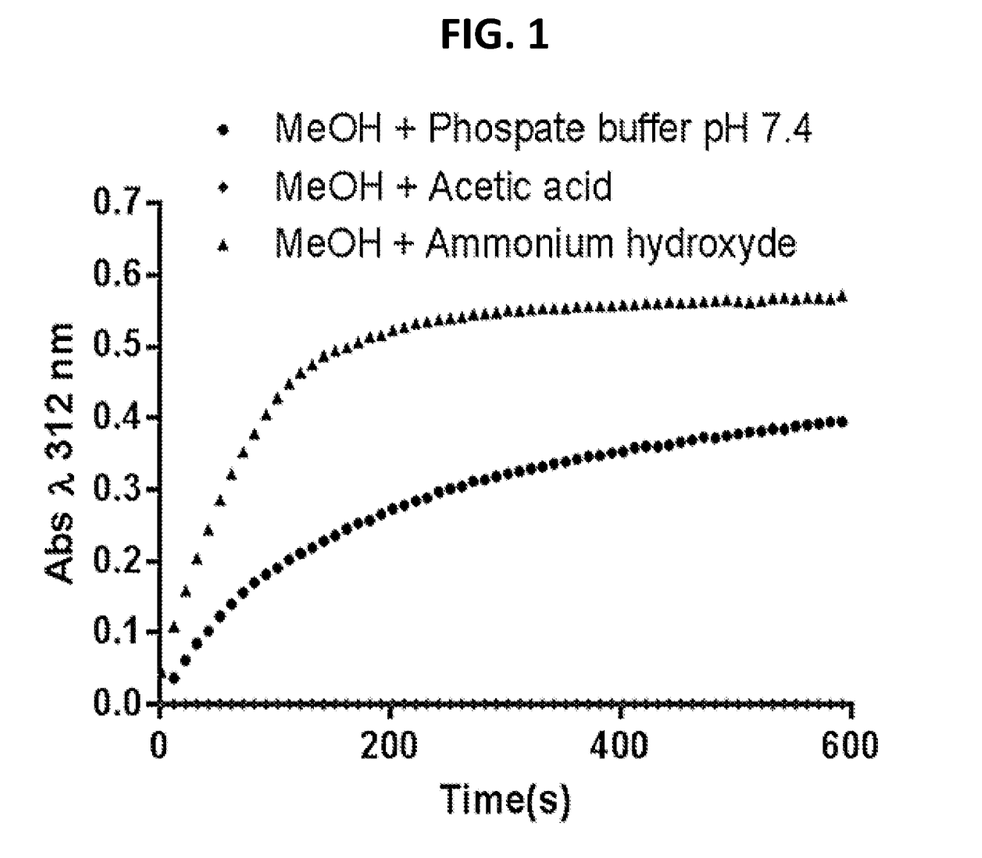
FIG. 1. UV-Vis analysis of $NO_2$-CLA generation by decomposition of nitrogen oxides of nitroalkenes ($NO_2$—$NO_3$-CLA). Kinetic analysis at different pH.

Synthetic $NO_2$—$NO_3$—CLA standards were generated by performing independent reactions of 0.5 mg conjugated-9, 11-linoleic acid (CLA, cat. no. UC-60A, Nu-Check Prep Inc., Elysian, Minn.) with 2 mM sodium nitrite ($NaNO_2$) in 1 ml artificial gastric fluid for 1 h at 37° C., under continuous agitation. The lipid fraction was extracted by hexane, 50 µl were dried under a stream of nitrogen gas, dissolved in 300 µl methanol and decomposition of the $NO_2$—$NO_3$—CLA with generation of $NO_2$-CLA was measured spectrophotometrically at 312 nm (FIG. 1). The addition of 10 µl acetic acid to the methanolic solution confirmed the stability of $NO_2$—$NO_3$—CLA at acidic pH (FIG. 1, diamond curve). Instead, the addition of 10 µl phosphate buffer 50 mM, pH 7.4 (FIG. 1, circle curve) or 10 µl ammonium hydroxide (FIG. 1, triangle curve) showed that the degradation of $NO_2$—$NO_3$—CLA was pH-dependent and a pH increase from pH 7.4 to more basic pH resulted in a faster generation of $NO_2$-CLA.

Figure 2A:
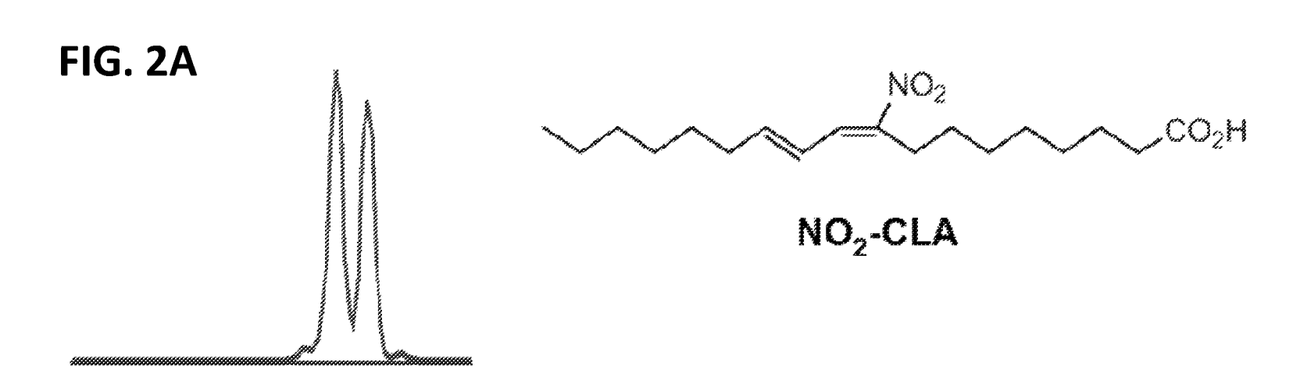
FIGS. 2A-2C. Mass spectrometry analysis of nitrated CLA products in rat gastric fluid after supplementation of CLA+$NO_2^-$. MRM chromatograms for: A) $NO_2$-CLA; B) $NO_2$—$NO_3$-CLA; C) MS2 analysis of $NO_2$—$NO_3$-CLA.
Figure 2B:
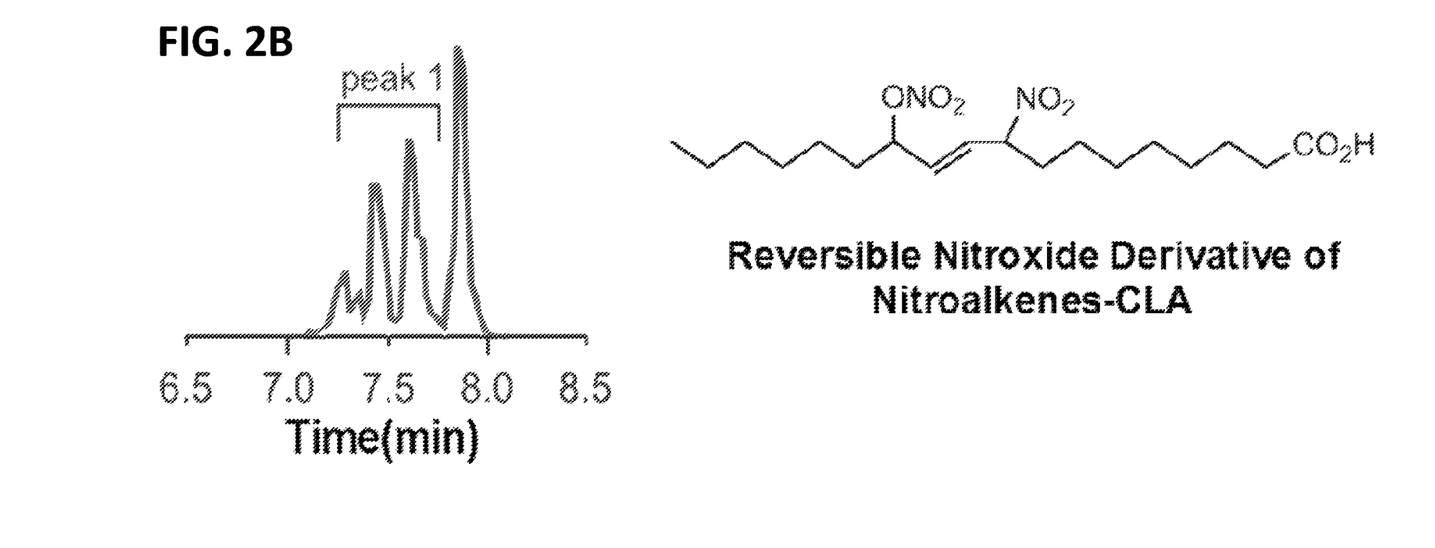
Figure 2C:
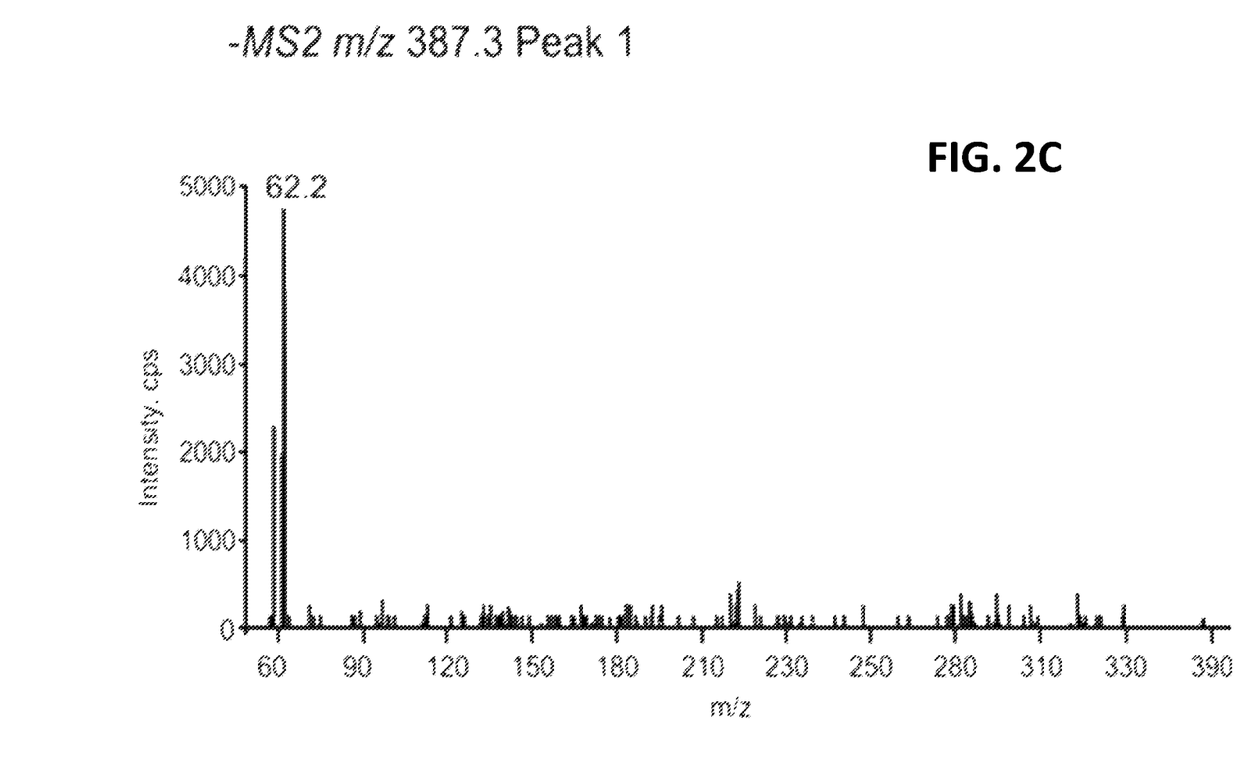

To investigate in vivo formation of $NO_2NO_3$-CLA, male Sprague-Dawley rats fasted overnight, treated with pentagastrin (50 µg/Kg i.p.), to stimulate gastric acid secretion, and after 20 minutes they were gavaged with CLA and $NO_2$— (100 µM) dissolved in polyethylene glycol. Then, after 1 hr the stomach was dissected out and the gastric juice was collected, centrifuged, and an equivalent volume of phosphate buffer 50 mM, pH 7.4 with 100 µM diethylenetriaminepentaacetic acid (DTPA) was added. The resultant solution was extracted with 1 ml hexane, dried under a stream of nitrogen gas, dissolved in 1 ml methanol and nitrated species were analyzed by high performance liquid chromatography-tandem mass spectrometry (HPLC-MS/MS) (FIG. 2).

Analysis of $NO_2$—$NO_3$—CLA was performed by HPLC-MS/MS using an analytical C18 Luna column (2×100 mm, 5 µm, Phenomenex) at a 0.6 ml/min flow rate, with a gradient solvent system consisting of water containing 0.1% acetic acid (solvent A) and acetonitrile containing 0.1% acetic acid (solvent B). Samples were chromatographically resolved using the following gradient program: 45-100% solvent B (0-8 min); 100% solvent B (8-10 min) followed by 2 min re-equilibration to initial conditions. $NO_2$—$NO_3$—CLA were detected using an API4000 Q-trap triple quadrupole mass spectrometer (Applied Biosystems, San Jose, Calif.) equipped with an electrospray ionization source (ESI) in negative mode. The following parameters were used: declustering potential, −75 V; collision energy, −35 eV; and a desolvation temperature of 650° C. $NO_2$—$NO_3$-CLA and the corresponding degradation product $NO_2$—CLA were analyzed using the following multiple reaction monitoring (MRM) transitions: 387.3/62 (FIG. 2A) and 324.3/46 (FIG. 2B), respectively. The $NO_2$—$NO_3$-CLA species were further structurally characterized via MS2 fragmentation. MS2 analysis of the peaks eluting from 7 to 7.7 min (FIG. 2A, peak 1) generated a specific nitrate ($NO_3$—) fragment m/z 62, which unequivocally confirmed the presence of $NO_2$—$NO_3$—CLA (FIG. 2C).

Figure 3:
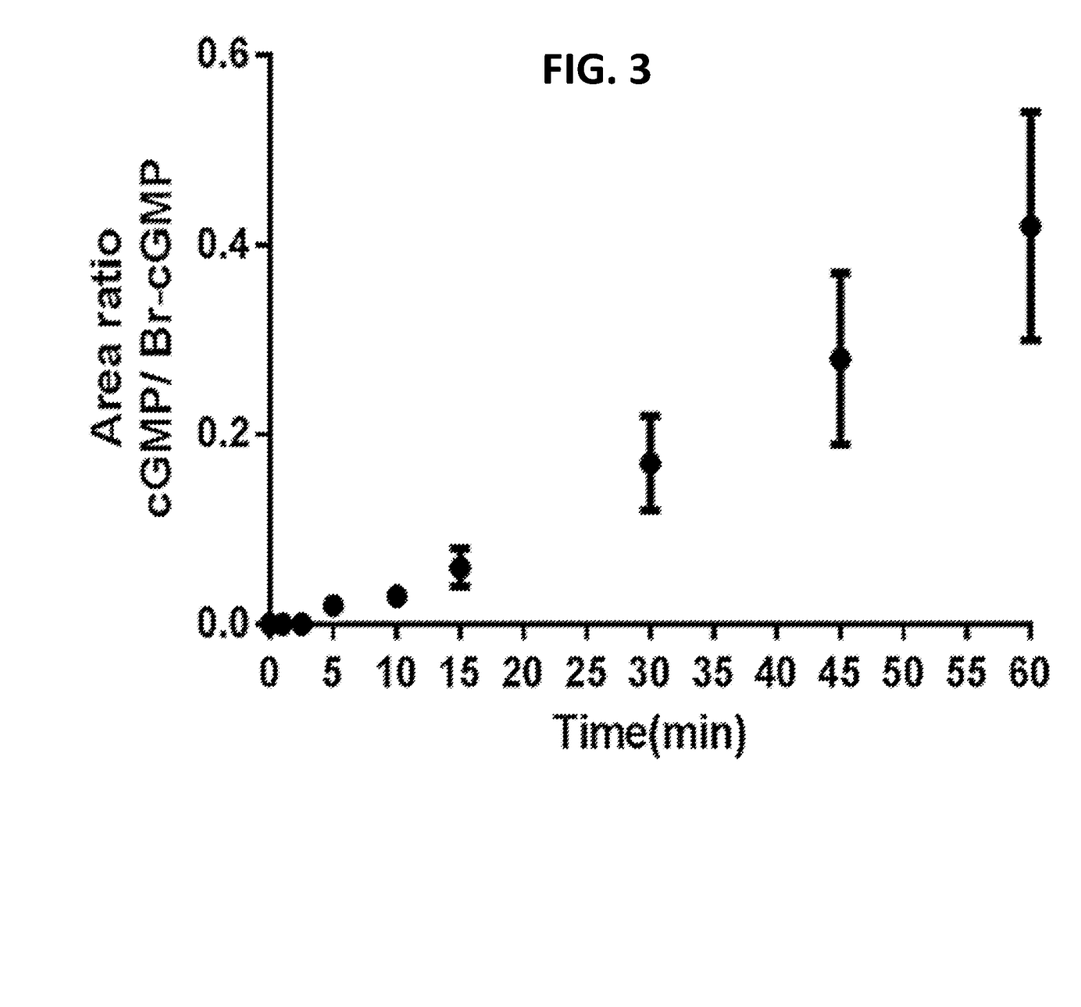
FIG. 3. Time dependent stimulation of soluble guanylate cyclase (sGC) activity via nitric oxide release from $NO_2$—$NO_3$—CLA-containing phosphatidylcholine. HPLC-MS/MS determination of cGMP formation after activation of sGC with $NO_2$—$NO_3$—CLA-containing phosphatidylcholine over 60 minutes. Data present means±SD of one replicate, subtracted sGC basal activity, of two independent experiments.

To investigate if $NO_2$—$NO_3$—CLA species were formed even when the acyl chain was esterified into complex lipids and if their degradation induced generation of nitric oxide, a CLA-containing phospholipid standard was nitrated under in vitro gastric conditions and a guanylyl cyclase activity assay was performed, respectively. 0.5 mg 1-Stearoyl-2-[9(Z), 11(E)-octadecadienoyl]-sn-glycero-3-phosphorylcholine (CLA-PC, cat. no. 1410, Matreya LLC, State College, Pa.) were incubated in presence of 2 mM $NaNO_2$ in 1 ml artificial gastric fluid for 1 h at 37° C., under continuous agitation, to generate $NO_2$—$NO_3$—CLA-containing phosphorylcholine. Then, 1 ml phosphate buffer 50 mM, pH 7.4 with 100 µM DTPA was added, lipid fraction was extracted with 1 ml hexane, 300 µl were dried under a stream of nitrogen gas and incubated over 60 minutes in 1 ml reaction buffer containing: Tris 50 mM, $MgCl2$ 3 mM, dithiothreitol (DTT) 0.01 mM, guanosine triphosphate (GTP) 1 mM, 0.05% bovine serum albumin (BSA), 50 ng/ml soluble guanylyl cyclase (sGC) at pH 7.4, and 2.5 nmol internal standard 8-bromoguanosine 3',5'-cyclic monophosphate (Br-cGMP). At each time point, 10 µl of the reaction solution were dissolved in 200 µl water 0.1% acetic acid and cyclic guanosine monophosphate (cGMP) was analyzed by HPLC-MS/MS (FIG. 3).

Analysis of cGMP was performed by HPLC-MS/MS using an analytical $C_{18}$ Luna column (2×150 mm, 3 µm, Phenomenex) at a 0.2 ml/min flow rate, with a gradient solvent system consisting of water containing 0.1% acetic acid (solvent A) and acetonitrile containing 0.1% acetic acid (solvent B). Samples were chromatographically resolved using the following gradient program: 10-80% solvent B (0-10 min); 100% solvent B (10-12 min) followed by 5 min re-equilibration to initial conditions. An API4000 Q-trap triple quadrupole mass spectrometer (Applied Biosystems, San Jose, Calif.), equipped with an electrospray ionization source (ESI) in negative mode, was used with the following parameters: declustering potential, −70 V; entrance potential −10; collision cell exit potential −10; and a desolvation temperature of 650° C. cGMP was analyzed using the following MRM transitions and collision energy (CE): 344.1/150.1, 344.1/133.1 with CE-35 and CE-50 respectively. Instead, the internal standard Br-cGMP was analyzed using the following MRM transitions and CE: 422.1/228.1, 422.1/211.1 with CE-35 and CE-50 respectively.

Figure 4:
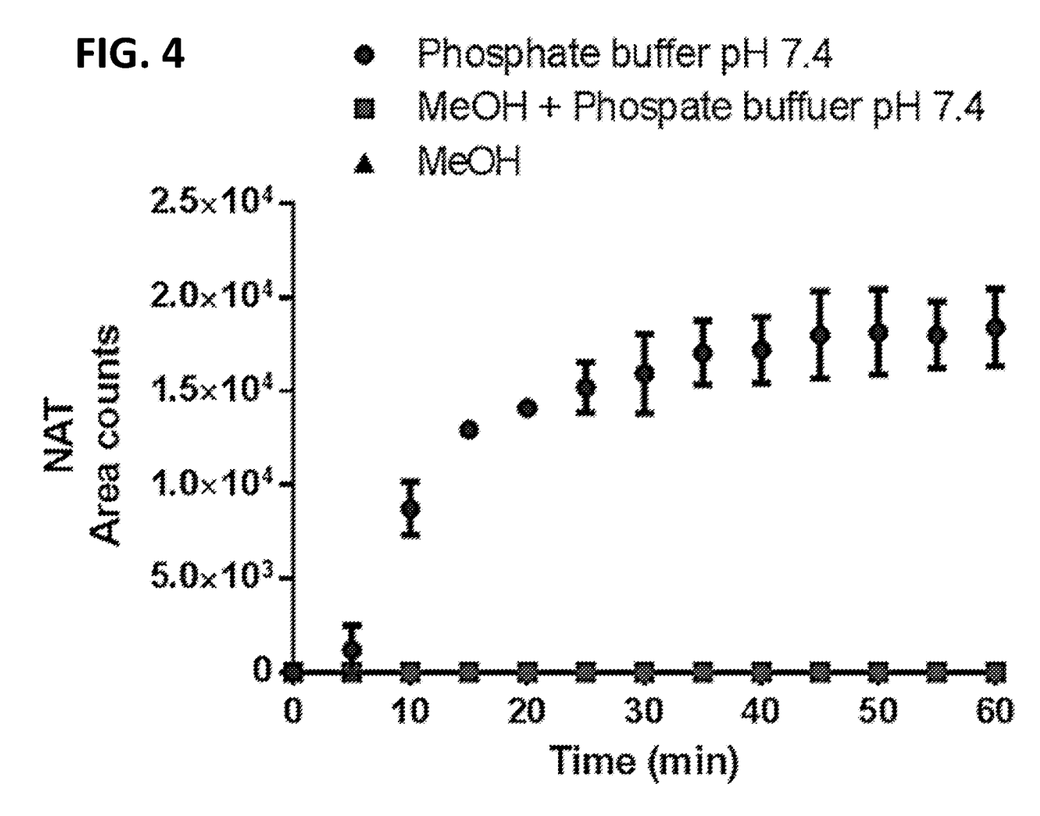
FIG. 4. NO and HNO release from $NO_2$—$NO_3$-CLA as followed by time dependent formation of naphthalene triazole (NAT) in presence of 2,3-diaminonaphthalene (DAN). NAT formation following reaction of 20 µM 2,3-DAN and $NO_2$—$NO_3$-CLA in solvents at different polarity. Data present means±SD of three replicates of one independent experiment.

To investigate if the degradation of NO$_2$—NO$_3$-CLA induced generation of nitrosative species, N-nitrosation of 2,3-diaminonaphtalene (DAN) to yield 2,3-naphthotriazole (NAT) was performed. Briefly, 25 µl synthetic NO$_2$—NO$_3$-CLA standards were dried under a stream of nitrogen gas, and resuspended in 1 ml of solvents at different polarity with 20 µM DAN. Then, formation of NAT was followed over 60 min by HPLC-MS/MS (FIG. 4). When NO$_2$—NO$_3$-CLA were dissolved in methanol none formation of NAT was observed (FIG. 4, square curve). Instead, the addition of 1 ml phosphate buffer 50 mM, pH 7.4 with 100 µM DTPA confirmed the instability of NO$_2$—NO$_3$-CLA in basic pH and showed time dependent generation of NAT (FIG. 4, circle curve).

Analysis of NAT was performed by HPLC-MS/MS using an analytical C18 Luna column (2×20 mm, 5 µm, Phenomenex) at a 0.75 ml/min flow rate, with a gradient solvent system consisting of water containing 0.1% acetic acid (solvent A) and acetonitrile containing 0.1% acetic acid (solvent B). Samples were chromatographically resolved using the following gradient program: 10-100% solvent B (0-3.3 min); 100% solvent B (3.3-4.2 min) followed by 0.8 min re-equilibration to initial conditions. An API4000 Q-trap triple quadrupole mass spectrometer (Applied Biosystems, San Jose, Calif.), equipped with an electrospray ionization source (ESI) in positive mode, was used with the following parameters: declustering potential, 70 V; entrance potential 5; collision cell exit potential 10; collision energy 35; and a desolvation temperature of 650° C. NAT was analyzed using the MRM transition 170.1/115.1.

What is claimed is:

1. A compound of Formula I:

(I)

wherein R$^1$ is —NO$_2$, R$^2$ is —ONO$_2$, X$^1$ is —H; and X$^2$ is —COOH; and m and n are, independently, an integer from 1 to 10.

2. The compound of claim 1, wherein the compound has a structure of:

3. A method of delivering nitric oxide comprising administering to a subject in need thereof an effective amount of the compound of claim 1.

4. The method of claim 3, wherein the compound has a structure of:

5. A method of treating inflammation, obesity, metabolic syndrome, acute kidney disease, or chronic kidney disease comprising administering to a subject in need thereof an effective amount of the compound of claim 1.

6. The method of claim 5, wherein negative side effects of a subject's gastrointestinal tract are reduced.

7. The method of claim 6, wherein the side effects of the gastrointestinal tract is selected from the group consisting of diarrhea, cramping irritation, inflammatory bowel disease, colitis, and ulcers.

8. The method of claim 5, wherein the compound has a structure of:

9. A method of inducing vasodilation comprising administering to a subject in need thereof an effective amount of the compound of claim 1.

10. The method of claim 9, wherein the compound has a structure of:

* * * * *